United States Patent [19]

Varn

[11] Patent Number: 5,569,173

[45] Date of Patent: Oct. 29, 1996

[54] FOOT ORTHOSIS WITH DETACHABLE SOLE PLATE

[75] Inventor: Harold T. Varn, Lawrenceville, Ga.

[73] Assignee: Restorative Care of America Incorporated, Clearwater, Fla.

[21] Appl. No.: 324,244

[22] Filed: Oct. 17, 1994

[51] Int. Cl.⁶ ...................................................... A61F 5/00
[52] U.S. Cl. ............................................................. 602/27
[58] Field of Search .............................. 602/3, 5, 27, 28, 602/29, 30, 60, 65; 36/12, 15, 23, 26, 104, 136, 71, 91, 110, 114, 131, 132

[56] References Cited

U.S. PATENT DOCUMENTS

| | | | |
|---|---|---|---|
| 3,416,518 | 12/1968 | Samuels et al. | 602/3 |
| 3,735,758 | 5/1973 | Novotney | 602/3 |
| 3,735,759 | 5/1973 | MacKay | 602/3 |
| 3,802,424 | 9/1974 | Newell | 602/3 |
| 3,878,626 | 4/1975 | Ishman | 36/15 |
| 4,289,122 | 9/1981 | Mason et al. | 602/27 |
| 4,887,369 | 12/1989 | Bailey et al. | 36/15 X |
| 4,974,344 | 12/1990 | Ching | 36/15 X |
| 5,052,128 | 10/1991 | Lonardo . | |
| 5,088,479 | 2/1992 | Detoro | 602/27 |
| 5,154,695 | 10/1992 | Farris et al. | 602/27 |
| 5,176,624 | 1/1993 | Kuehnreich | 36/15 X |
| 5,298,013 | 3/1994 | Lonardo . | |
| 5,317,822 | 6/1994 | Johnson | 36/15 |

Primary Examiner—Richard J. Apley
Assistant Examiner—Kim M. Lee
Attorney, Agent, or Firm—Zarley, McKee, Thomte, Voorhees, & Sease

[57] ABSTRACT

A foot orthosis has a generally L-shaped member to support the lower leg and foot of a patient. A flexible boot member is on the L-shaped member and is adapted to receive the leg and the foot a patient. The L-shaped member has a foot portion with a bottom surface with the boot member substantially extending over the bottom surface of the L-shaped member. A first releasable interlocking surface is on the portion of the boot member extending over the bottom surface of the L-shaped member. A resilient sole member having a second releasable interlocking surface thereon is releasably secured to the first releasable interlocking surface whereby the sole member can be removed from the boot member.

2 Claims, 3 Drawing Sheets

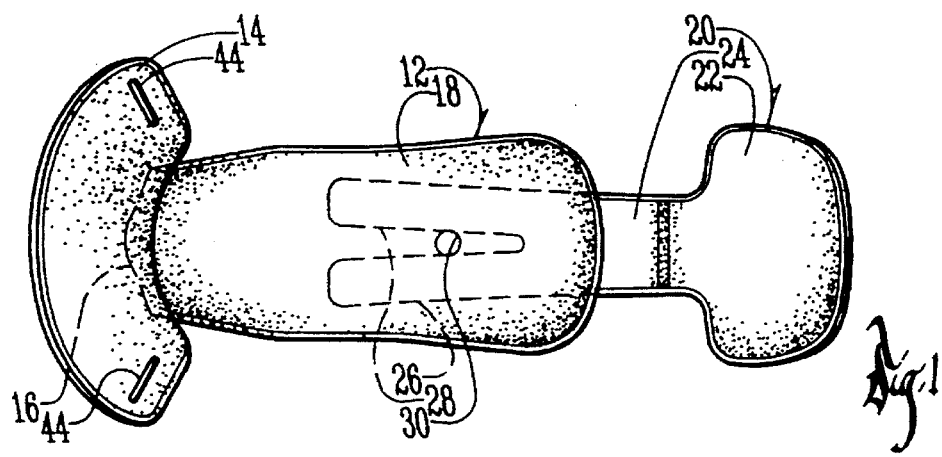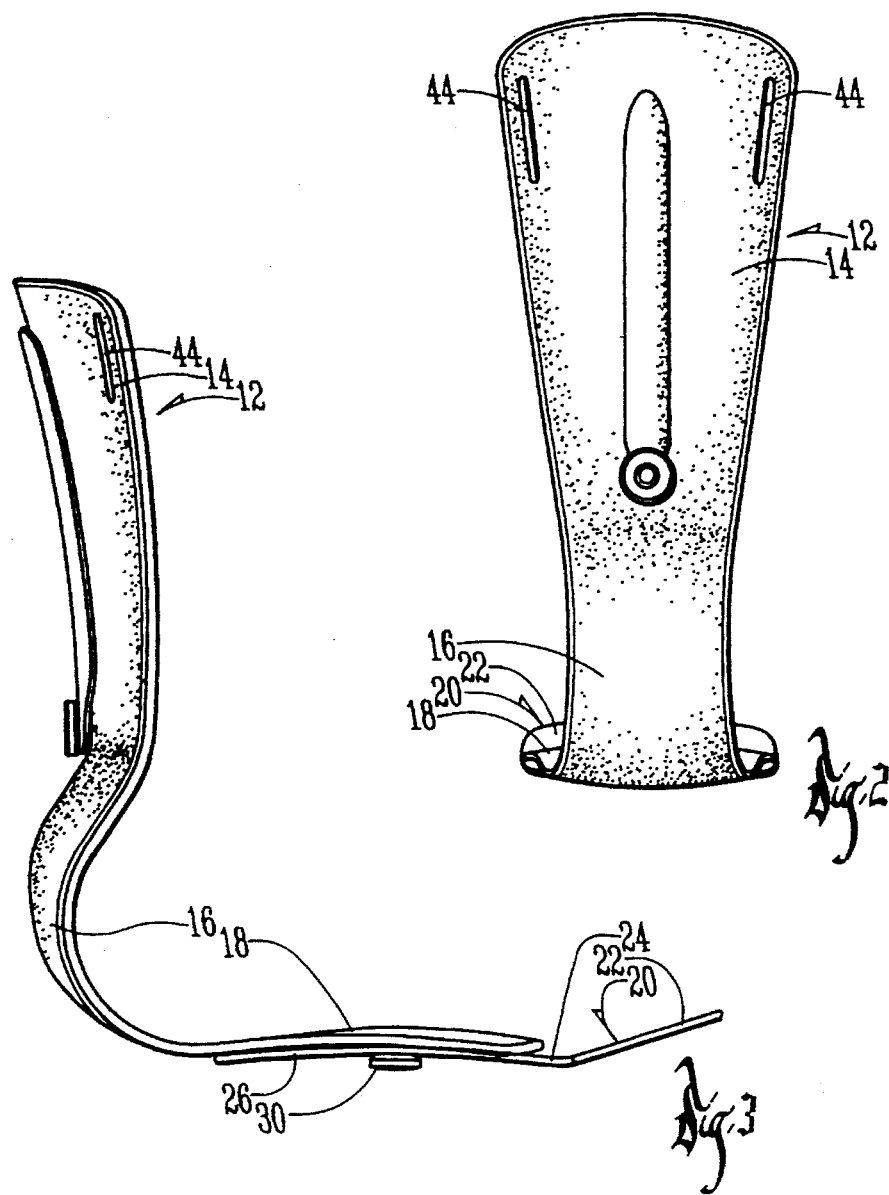

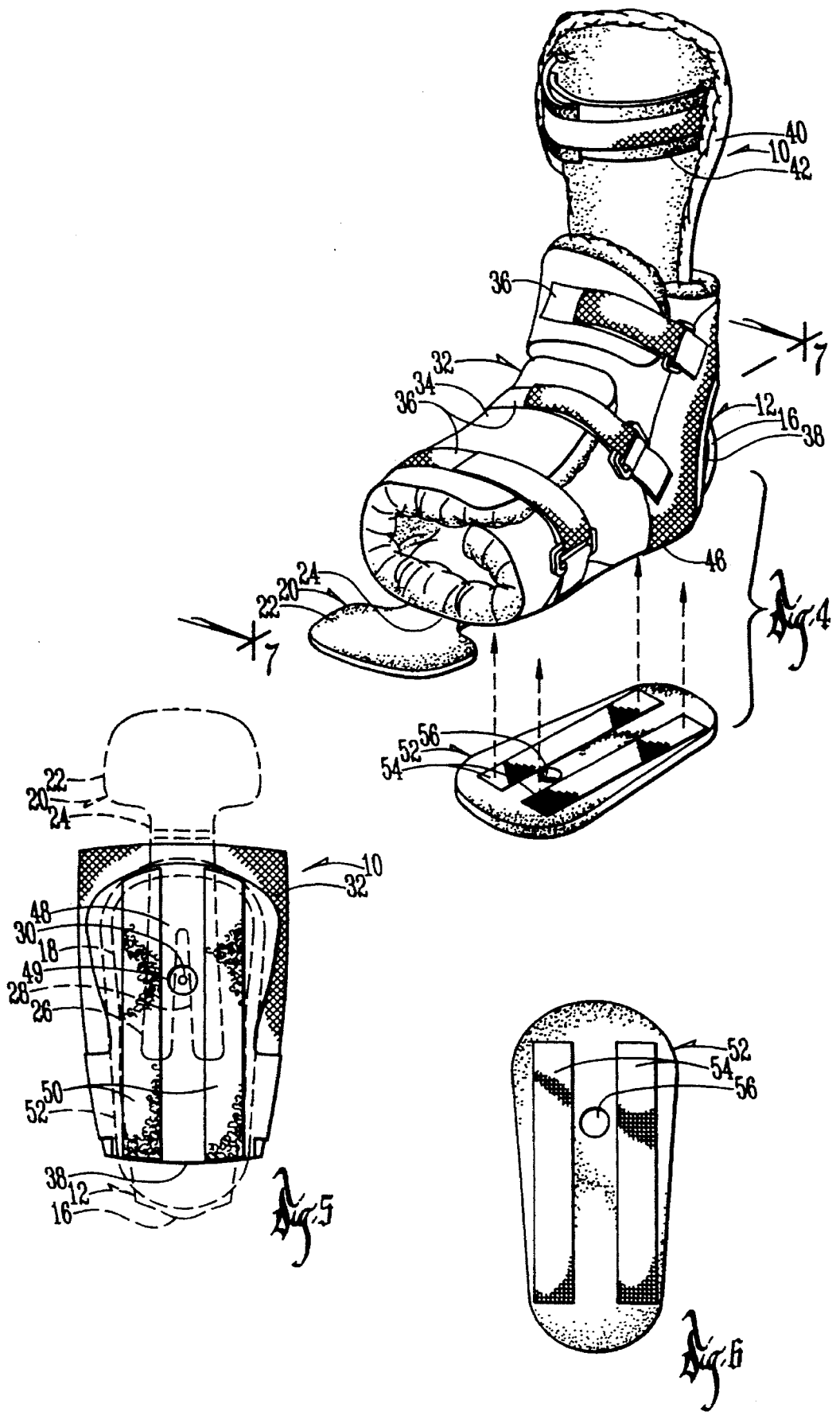

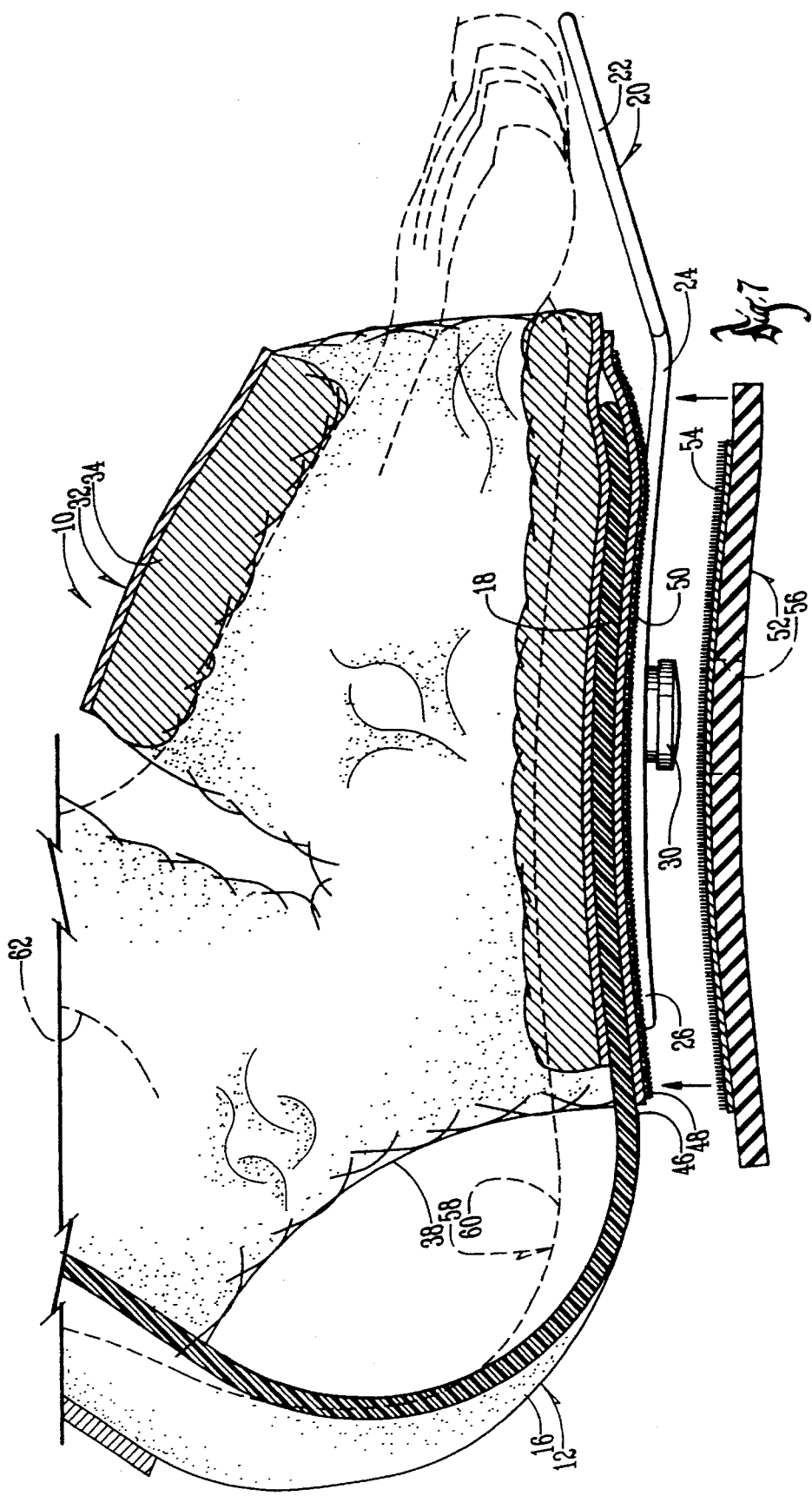

5,569,173

FOOT ORTHOSIS WITH DETACHABLE SOLE PLATE

BACKGROUND OF THE INVENTION

Foot orthosis such as that shown in U.S. Pat. No. 5,298,013 are comprised of an L-shaped splint having a leg portion, an enlarged heel portion, and a foot portion. The device has an anklet or boot which surrounds the patient's foot and/or leg and secures the foot and leg to the L-shaped splint device. These orthosis have been very useful in preventing bedsores on the heels of patients and in treating foot drop and other such maladies often suffered by bedfast patients.

The foregoing orthosis can be worn by not only bedfast patients but ambulatory patients or patients that can be moved in wheelchairs when they are out of bed. However, infection control regulations for hospitals and nursing homes often require that items that come in contact with the floor should not be returned to the patient's bed.

It is therefore a principal object of this invention to provide a non-skid sole plate which can be easily attached to a foot orthosis to allow a patient to do a stand up transfer from a bed to a chair or wheelchair and which will also accommodate a patient who is capable of walking with the orthosis in place.

It is a further object of this invention to provide a sole plate for an orthosis which can be easily detached and attached to the orthosis so that it can be removed when the patient returns to bed, but then easily reattached when the patient leaves the bed.

These and other objects will be apparent to those skilled in the art.

SUMMARY OF THE INVENTION

This invention pertains to a typical foot orthosis having an L-shaped member to support the lower leg and foot of a patient, and having a flexible boot member on the L-shaped member which is adapted to receive the leg and foot of the patient. The L-shaped member has a foot portion with a bottom surface with the boot member substantially extending over the bottom surface of the L-shaped member. A sole plate is detachably secured to the portion of the boot member which extends over the bottom surface of the L-shaped member by means of compatible strips of Velcro® fasteners which are secured to the bottom of the boot member and the top of the sole plate, respectively.

BRIEF DESCRIPTION OF THE DRAWINGS

FIG. 1 is a top plan view of the flexible plastic splint of a foot orthosis;

FIG. 2 is a rear elevational view of the device of FIG. 1;

FIG. 3 is a side elevational view of the device of FIG. 2;

FIG. 4 is a schematic perspective view of the device of FIGS. 1–3 with the boot mounted thereon and with the detachable sole plate spaced from the bottom of the orthosis;

FIG. 5 is a bottom elevational view of the boot of FIG. 4;

FIG. 6 is a top plan view of the detachable sole plate; and

FIG. 7 is an enlarged scale sectional view taken on line 7—7 of FIG. 4.

DESCRIPTION OF THE PREFERRED EMBODIMENT

A conventional foot orthosis 10 has an L-shaped flexible splint 12 having leg portion 14, an enlarged heel portion 16 and a foot portion 18. A toe brace 20 with an enlarged forward end 22 has a narrow arm portion 24 which terminates in a rearward end 26. An elongated notch 28 appears in rearward end 26 and receives nut and bolt assembly 30 which is rotatably and fixedly extending downwardly from the foot portion 18.

A boot or sandal 32 having a top access flap 34 envelops the foot orthosis 10 and receives the foot, ankle and/or leg of a patient. Straps 36 are used to secure the boot 32 to the foot and ankle of the patient. An opening 38 is provided in boot 32 at the heel portion thereof to permit lateral visual access to the enlarged heel portion 16 so that a patient's heel with a sore thereon can be visually observed as it is suspended in spaced relation to the enlarged heel portion 16. A conventional leg pad 40 is mounted on the leg portion 14 of the foot orthosis and a strap 42 is inserted through notch openings 44 in the leg portion 14 of the orthosis to secure both the splint 12 and the pad to the leg of the patient.

All of the foregoing structure is conventional and does not of itself comprise the essence of the instant invention.

The numeral 46 (FIG. 7) designates the bottom surface of the foot portion 18, and the numeral 48 designates the bottom layer of the boot which embraces the bottom surface 46 of the foot portion. A hole 49 is located in the bottom layer 48 of the boot to provide access to the nut and bolt assembly 30.

As best shown in FIG. 5, a pair of Velcro® straps 50 are longitudinally positioned and secured on the bottom surface 48 of boot 32. A flexible sole plate 52 has a pair of complimentary Velcro® straps 54 which are adapted to mate with the straps 50 and to be detachably secured thereto. A hole 56 in sole plate 56 registers with the hole 49 in the bottom layer 48 of the boot so as to provide further access to nut and bolt assembly 30. Sole plate 52 should have a non-skid texture on its lower surface (not shown).

The numeral 58 designates a patient's foot having a heel 60, and an ankle 62.

In operation, the sole plate 52 as shown in FIG. 4 can be moved upwardly to engage straps 50 so as to permit the Velcro® straps 54 thereon to overlap and detachably engage the Velcro® straps 50 on the bottom surface of the bottom layer 48 of boot 32. After this has been done, the patient can move or be moved from a position in the bed to a walking position or transportation position remote from the bed. When the patient is returned to the bed, the above procedure can be reversed whereby the sole plate is detachably removed from the boot by physically pulling the sole plate 52 downwardly so as to separate the Velcro® straps 50 and 54.

It is therefore seen that this invention will permit the foot orthosis 10 to be used by the patient in bed whereupon the patient, after the sole plate is attached, can depart from the bed and return thereto by reason of the ability of the sole plate to be detached from the orthosis before the patient reenters the bed. It is thus seen that this invention will achieve at least its stated objectives.

What is claimed is:

1. A foot orthosis, comprising, a generally L-shaped member to support the lower leg and foot of a patient, a flexible boot member on said L-shaped member adapted to receive the leg and a foot of a patient, said L-shaped member having a foot portion with a bottom surface, said boot member having a bottom surface portion substantially extending over said bottom surface of said L-shaped member, a first releasable interlocking surface on the bottom surface portion of said boot member which extends over the bottom surface of said L-shaped member, and a resilient foot sole member releasably secured to the bottom surface portion of said boot member, said foot sole member having a second releasable interlocking surface thereon releasably secured to said first releasably interlocking surface on the bottom surface portion of said boot member whereby said foot sole member can be removed from said boot member.

2. The device of claim 1 wherein means are provided on said boot member for securing a patient's leg and foot within said boot member.

* * * * *